United States Patent
Yu (10) Patent No.: US 9,984,184 B2
(45) Date of Patent: May 29, 2018

(54) BIOLOGICAL NETWORK ANALYSIS DEVICE AND METHOD THEREFOR

(71) Applicant: KOREA INSTITUTE OF SCIENCE AND TECHNOLOGY INFORMATION, Daejeon (KR)

(72) Inventor: Seok Jong Yu, Cheongju-si (KR)

(73) Assignee: KOREA INSTITUTE OF SCIENCE AND TECHNOLOGY INFORMATION, Daejeon (KR)

(*) Notice: Subject to any disclaimer, the term of this patent is extended or adjusted under 35 U.S.C. 154(b) by 540 days.

(21) Appl. No.: 14/404,089

(22) PCT Filed: Sep. 3, 2014

(86) PCT No.: PCT/KR2014/008225
§ 371 (c)(1),
(2) Date: Nov. 26, 2014

(87) PCT Pub. No.: WO2015/099264
PCT Pub. Date: Jul. 2, 2015

(65) Prior Publication Data
US 2016/0283626 A1    Sep. 29, 2016

(30) Foreign Application Priority Data
Dec. 27, 2013  (KR) .................. 10-2013-0165128

(51) Int. Cl.
G06G 7/58       (2006.01)
G06F 17/50      (2006.01)
G06F 19/12      (2011.01)
G06F 17/30      (2006.01)

(52) U.S. Cl.
CPC .... *G06F 17/5022* (2013.01); *G06F 17/30477* (2013.01); *G06F 19/12* (2013.01)

(58) Field of Classification Search
CPC .................................................. G06F 17/5022
USPC .......................................................... 703/11
See application file for complete search history.

(56) References Cited

U.S. PATENT DOCUMENTS

| 7,856,317 | B2 | 12/2010 | Schilling | 702/19 |
| 2003/0225718 | A1* | 12/2003 | Shmulevich | G06F 19/12 706/46 |
| 2004/0088116 | A1* | 5/2004 | Khalil | G06F 19/12 702/20 |
| 2007/0174019 | A1 | 7/2007 | Vailaya et al. | 702/179 |
| 2010/0299289 | A1 | 11/2010 | Simya et al. | 706/12 |
| 2013/0096888 | A1* | 4/2013 | Hickman | G01N 33/5058 703/2 |

FOREIGN PATENT DOCUMENTS

KR   10-2009-0105921 A   10/2009
KR   10-1067352 B1   9/2011

OTHER PUBLICATIONS

Cunningham et al., "Getting More Out of Biomedical Documents with GATE's Full Lifecycle Open Source Text Analytics" PLOS Computational Biology (Feb. 2013) vol. 9, issue 2, pp. 1-16.*
International Search Report and Written Opinion dated Oct. 30, 2014 issued in Application No. PCT/KR2014/008225.

* cited by examiner

*Primary Examiner* — Jerry Lin
(74) *Attorney, Agent, or Firm* — Ked & Associates, LLP

(57) ABSTRACT

The present invention relates to a biological network analysis device and a method therefor. The biological network analysis method includes receiving biological data from an external server, extracting biological information from the received biological data to generate a biological interaction database, storing the generated biological interaction database, receiving input of a plurality of biological objects for a simulation, and performing a simulation by setting each of the biological objects to a node and automatically and generating a Boolean role based on the generated biological interaction database. Accordingly, the biological network analysis method conveniently designs a biological network and simulates the biological network based on biological interaction information by generating the biological interaction database.

17 Claims, 6 Drawing Sheets

BIOLOGICAL NETWORK ANALYSIS DEVICE AND METHOD THEREFOR

CROSS-REFERENCE TO RELATED PATENT APPLICATIONS

This application is a U.S. National Stage Application under 35 U.S.C. § 371 of PCT Application No. PCT/KR2014/008225, filed Sep. 3, 2014, which claims priority to Korean Patent Application No. 10-2013-0165128, filed Dec. 27, 2013, whose entire disclosures are hereby incorporated by reference.

TECHNICAL FIELD

The present invention relates to a biological network analysis device and a method therefor, and more particularly, to a biological network analysis device and a method therefor to simulate and analyze a biological network.

BACKGROUND ART

In the life sciences, study into reaction to external stimuli is a key area of research. Such research is called signaling pathway research. To generate such signaling pathways, signaling pathways are built by confirming and extending interaction between proteins based on individual biological experiments. KEGG, BioCarta, BioCyc and the like provides information for signaling pathways which is collected and databased.

To confirm biological facts, it is key to extend pathways or establish a hypothesis for new interaction in pathways based on signaling pathways discovered from prior studies. To support this, simulation is conducted using a numerical analysis method. As a representative example, there is ordinary differential equation (ODE) analysis, which is broadly used in metabolic engineering, for a metabolic network. However, since a rate constant of chemical reaction for interaction between each protein in a signaling process is not known in most cases, applicability of ordinary differential equation (ODE) analysis is limited.

Therefore, although all information is not known, the need for technology which may simply design and simulate a biological network is emerging.

DISCLOSURE

Technical Problem

An object of the present invention devised to solve the problem lies in a biological network analysis device and a method therefor to conveniently design and simulate a biological network based on biological interaction information.

Technical Solution

The object of the present invention can be achieved by providing a biological network analysis device including a communication unit receiving biological data from an external server, a controller extracting the biological information from the received biological data to generate a biological interaction database, a storage unit storing the generated biological interaction database, and an input unit receiving input of a plurality of biological objects for a simulation, wherein the controller sets each of the input biological objects to a node and automatically generates a Boolean role based on the generated biological interaction database to perform a simulation.

In addition, the biological network analysis device may further include an output unit to output at least one of the generated biological interaction database and the performed simulation result.

In addition, the controller may analyze a sentence structure from the received biological data, may extract biological interaction words and biological object words from the analyzed sentence structure, may judge the biological interaction between extracted biological object words and may extract the biological information including the biological object information and the biological interaction information, to generate the biological interaction database.

Alternatively, the controller may set a first node and a second node receiving input from the first node, and may set the Boolean role using the biological interaction information between the biological object information of the first node and the biological object information of the second node.

In addition, the controller may individually set the Boolean role in accordance with each node.

Alternatively, the controller may update a connection state between the nodes by applying a preset probability to perform simulation.

In another aspect of the present invention, provided herein is a biological network analysis method including receiving biological data from an external server, extracting biological information from the received biological data to generate a biological interaction database, storing the generated biological interaction database, receiving input of a plurality of biological objects for a simulation, and performing a simulation by setting each of the biological objects to a node and automatically generating a Boolean role based on the generated biological interaction database.

In addition, the biological network analysis method may further include outputting the generated biological interaction database.

Alternatively, the biological network analysis method may further include outputting the performed simulation result.

Meanwhile, the generating includes analyzing a sentence structure from the received biological data, extracting biological interaction words and biological object words from the analyzed sentence structure, judging the biological interaction relation between the extracted biological object words, and extracting the biological information including biological object information and biological interaction information, to generate the biological interaction database.

In addition, the performing may set a first node and a second node receiving input from the first node, and may set the Boolean role using biological interaction information between biological object information of the first node and biological object information of the second node.

Alternatively, the performing may be individually set the Boolean role in accordance with each node.

In addition, the performing may update a connection state between nodes by applying a preset probability to perform the simulation.

Advantageous Effects

As is apparent from the above description, a biological network analysis device and a method therefor can conveniently design and simulate a biological network based on biological interaction information by generating a biological interaction database.

BEST MODE

Reference will now be made in detail to the preferred embodiments of the present invention, examples of which are illustrated in the accompanying drawings. The features of the present invention will be more clearly understood from the accompanying drawings and should not be limited by the accompanying drawings.

Most of the terms used herein are general terms that have been widely used in the technical art to which the present invention pertains. However, some of the terms used herein may be created reflecting intentions of technicians in this art, precedents, or new technologies. Additionally, some of the terms used herein may be arbitrarily chosen by the present applicant. In this case, these terms are defined in detail below. Accordingly, the specific terms used herein should be understood based on the unique meanings thereof and the overall context of the present invention.

Figure 1:
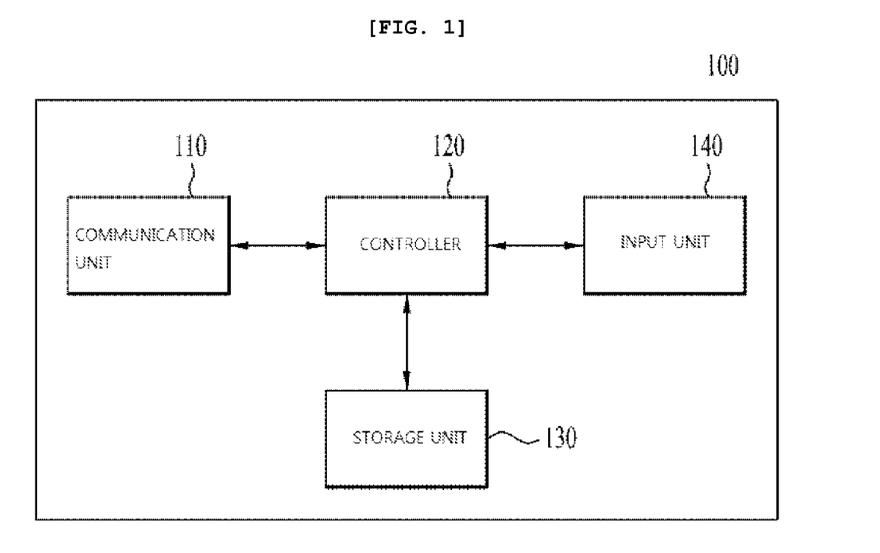
FIG. 1 is a block view of a biological network analysis device according to one embodiment of the present invention.

FIG. 1 is a block view of a biological network analysis device according to one embodiment of the present invention.

Referring to FIG. 1, a network analysis device 100 includes a communication unit 110, a controller 120, a storage unit 130, and an input unit 140.

The communication unit 110 receives biological data from an external server. Biological data means scientifically proved data such as study results or experimental results in the life sciences. Biological data may include biological object information such as proteins, genes, titles of cells and the like, and information on a relationship between biological objects such as activation, suppression, control and the like. Information on a relationship between biological objects is also called biological interaction information. The communication unit 110 connects the biological network analysis device 100 to an external server (not shown) using wired/wireless communication.

The controller 120 extracts biological information from received biological data to generate a biological interaction database. The biological data may include biological object information and biological interaction information described above, and a variety of information or data. Accordingly, the controller 120 extracts biological information from biological data. The biological information includes biological object information and biological interaction information.

The controller 120 analyzes a sentence structure from received biological data to extract biological interaction words and biological object words from the analyzed sentence structure. The controller 120 judges biological interaction between extracted biological object words to extract biological information including the biological object information and the biological interaction information. The controller 120 generates a biological interaction database with the extracted biological information.

In addition, when the controller 120 receives input of a simulation performance command from a user, the controller 120 performs simulation using the generated biological interaction database. That is, the controller 120 sets each of input plural biological objects to a node and automatically generates a Boolean role based on the generated biological interaction database to perform a simulation. For example, the Boolean role means a method of setting interrelation between biological objects using logical arithmetic. The logical arithmetic means AND, OR, NOT and the like. The Boolean role may be individually set in accordance with each node.

The controller 120 sets a first node and a second node as a form receiving input from the first node in accordance with input of a user. The controller 120 may set a Boolean role using biological interaction information between biological object information of the first node and biological object information of the second node. In addition, the controller 120 updates a connection state between nodes based on a preset probability to perform a simulation.

The storage unit 130 stores the generated biological interaction database. For example, the storage unit 130 may include a main memory unit such as a RAM, ROM or the like, a hard disk (HDD), and a secondary memory unit such as a solid state drive (SDD), a compact disc (CD), a digital versatile disc (DVD), a Bluray disc (BD), a USB memory, an SD card, a memory stick, a CF card, an MMC card, a Zip drive, a Jaz drive, a magnetic tape or the like.

The input unit 140 receives input of a plurality of biological objects for a simulation. For example, the input unit 140 may be realized through an image input unit such as a keyboard, a mouse, a joystick, a button, a camera or the like, a voice input unit such as a microphone or the like, a touch pad, a touch-screen, or the like.

Figure 2:
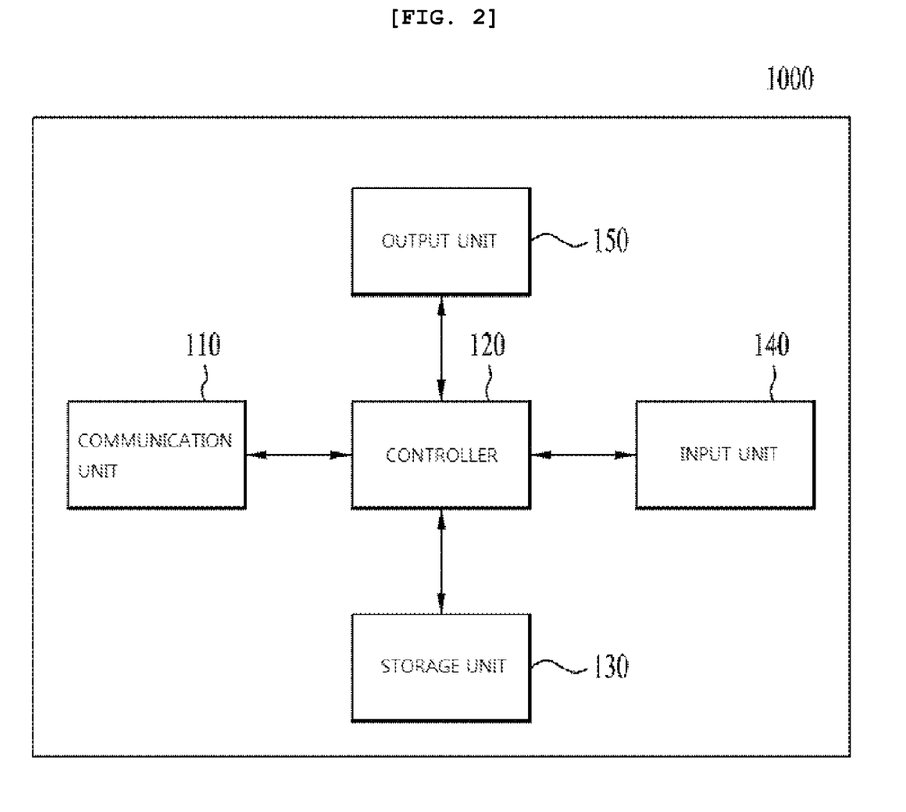
FIG. 2 is a block view of a biological network analysis device according to another embodiment of the present invention.

FIG. 2 is a block view of a biological network analysis device according to another embodiment of the present invention.

Referring to FIG. 2, a biological network analysis device 100a may include the communication unit 110, the controller 120, the storage unit 130, the input unit 140, and an output unit 150. The communication unit 110, the controller 120, the storage unit 130, and the input unit 140 are similar to those described in FIG. 1 and description below is given in conjunction with the output unit 150.

The output unit 150 may output at least one of the generated biological interaction database and the performed simulation result. That is, the output unit 150 may output the generated biological interaction database. The biological interaction database is generated by extracting biological information from received biological data. The biological information may include biological object information and biological interaction information. Accordingly, the controller 120 may judge related second biological object information from first biological object information and may judge a relation between a first biological object and the second biological object. The controller 120 may generate a biological interaction graph or a network based on the first biological object, the second biological object, and a relation between the first biological object and the second biological object. The output unit 150 may output the generated biological interaction graph or network.

In addition, the output unit 150 may output the performed simulation result. The controller 120 may simulate a signaling process between the first biological object and the second biological object selected from the biological interaction database. The simulation may be performed using biological interaction information between the biological objects through Boolean role set. The performed simulation result may be output from the output unit 150.

Regarding the biological interaction graph or the network, and the simulation, only two biological objects are described as an example but three or more biological objects may be included. Up to now, a block view of biological network analysis device was described. Hereinafter, a biological interaction database and a biological interaction simulation will be described.

Figure 3:
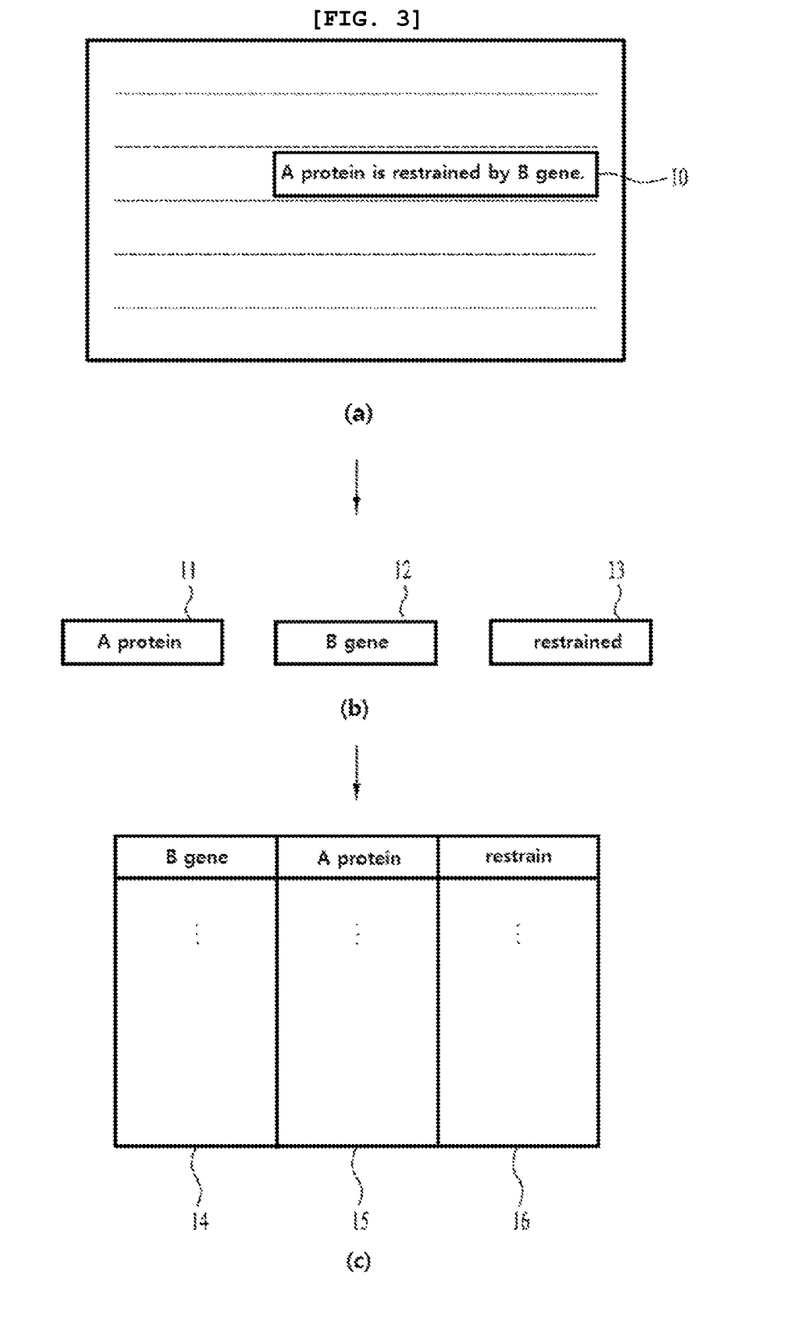
FIG. 3 illustrates a process of generating a database according to one embodiment of the present invention.

FIG. 3 illustrates a process of generating a database according to one embodiment of the present invention.

In FIG. 3(*a*), one paper was illustrated. Biological data may be extracted from a research result such as journal articles, literature, reports or the like. For example, abstract information may be downloaded from a literature database based on a keyword. Literature analysis may be performed by dividing an abstract of each paper into each sentence and analyzing the sentence structure. As one embodiment, the biological network analysis device divides a sentence 10, namely, "A protein is restrained by B gene.", and then extracts a verb having biological interaction information in the sentence. The biological network analysis device extracts a biological object as a subject and a biological object as an object based on the verb. Through such a process, it is recognized that biological words such as protein A or gene B are included. Through this, biological object information and biological interaction information may be extracted.

In FIG. 3(*b*), extracted biological object words and extracted biological interaction words are illustrated. In the embodiment described above, biological network analysis device may extract "restrained 13", which is a verb, and "protein A 11" and "gene B 12", which are biological objects. In this process, a biological tagger may be used to extract biological terms. For example, a glossary such as Metamap including approximately 133 term fields and Abner including mainly proteins, genes and cellular names may be used. Through such a process, biological information including biological objects and biological interaction information may be extracted. The biological network analysis device generates a biological interaction database.

In FIG. 3(*c*), the generated biological interaction database is illustrated. As one embodiment, the biological interaction database may be generated in a form including two biological objects and interaction information between the biological objects. In the embodiment described above, the biological interaction database may be generated in a form including a frist region including a B gene 14, a second region including an A protein 15, and a third region including "restrain" as interaction information 16.

In addition, the biological interaction database may further include additional information. For example, the additional information may be information such as a reaction constant, reaction time, an activation condition, a suppression condition, a control condition or the like, which are related to interaction between biological objects.

The generated biological interaction database may be output in a form which may be non-logically realized such as a graph or a network.

Figure 4:
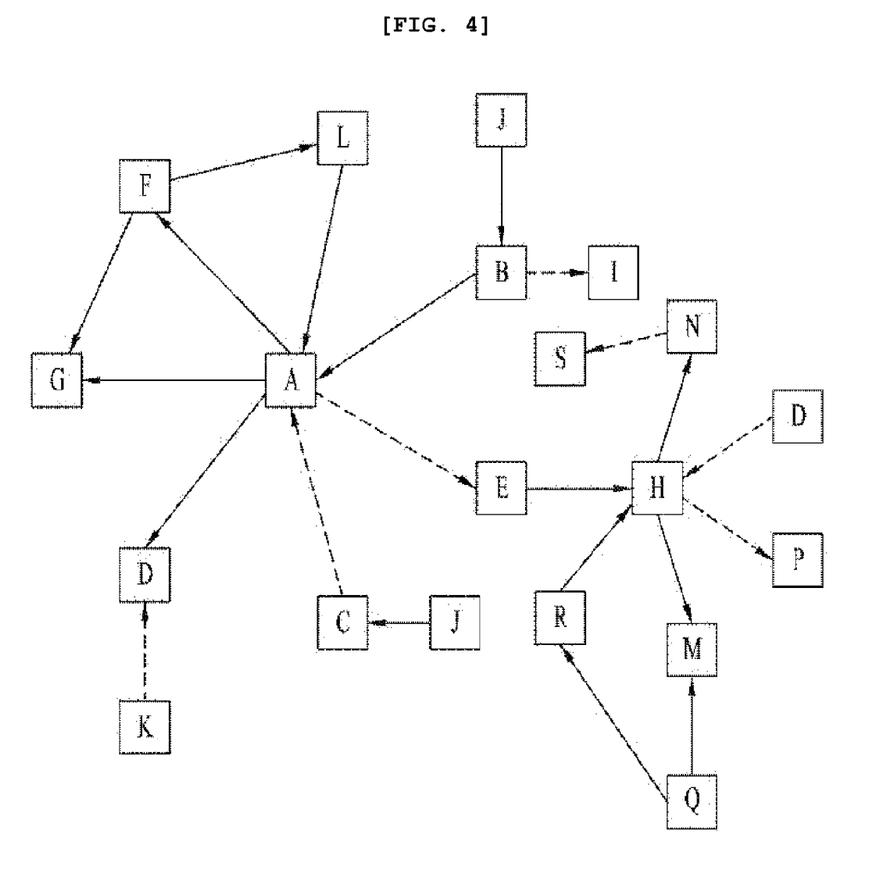
FIG. 4 illustrates a generated database according to one embodiment of the present invention.

FIG. 4 illustrates a database according to one embodiment of the present invention.

Referring to FIG. 4, a biological interaction database, which is output to a network type, is illustrated. As one embodiment, biological objects such as A, B, C and the like may be displayed in a quadrangle. When the biological object A affects the biological object B, an interaction relation therebetween may be indicated by an arrow. An activation interaction relation may be indicated by a solid line and an inhibition interaction relation may be indicated by a dotted line. A biological interaction database of a network type illustrated in FIG. 4 is one embodiment and may be realized through a variety of methods. For example, in accordance with a classification standard of biological objects, the biological objects may be displayed in a shape such as a circle, a quadrangle, a triangle or the like, and in a color such as yellow, red, blue or the like. The biological interaction information may also be displayed in a variety of types such as color, thickness or the like, in accordance with a constant standard.

Figure 5:
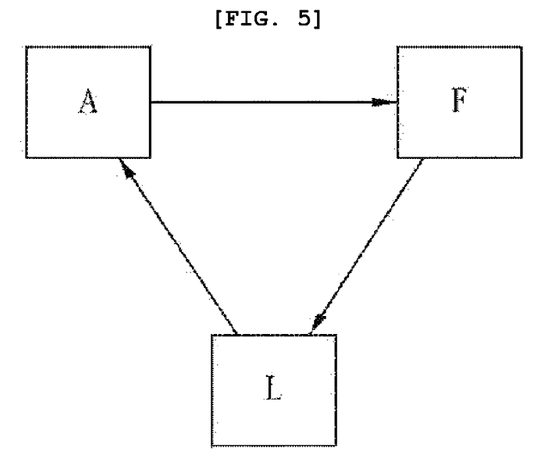
FIG. 5 illustrates a simulation process according to one embodiment of the present invention.

FIG. 5 illustrates a simulation process according to one embodiment of the present invention.

Referring to FIG. 5, biological objects and biological interaction information between the biological objects are illustrated. That is, FIG. 5 is a model illustrating that A affects F, F affects L and L affects A. For example, when a user selects a biological object such as A, F, or L, the biological network analysis device may model biological objects selected from the biological interaction database and an interaction relation between the biological objects. Each biological object such as A, F, and L is called a node.

As one embodiment, a Boolean role generated in each node may be divided into a fixed portion and a changeable portion. The fixed portion is an unchanged portion as a common portion between biological objects and the changeable portion may be interaction information changed in accordance with each biological object. Accordingly, the biological network analysis device may previously generate a Boolean role of a basic type including the fixed portion and the changeable portion. In addition, the biological network analysis device may perform a Boolean role by defining a changeable portion in accordance with a biological model, which is modeled by a user, based on a biological interaction database generated through text mining.

In some cases, when a biological object, which may not be modeled by a user, is selected, the biological network analysis device may output a notice message or an error message. When the biological network analysis device receives input of a simulation performance command after modeling, the biological network analysis device may perform a simulation and may output a result.

The present invention approximately simulates a control mechanism of a biological network using a boolean network analysis method. Boolean network analysis determines whether each node is activated or inactivated in accordance with a condition of an existing input node and a control mechanism of a biological network may be determined using a Boolean role of each node. Such a role is called a transfer function. As a role to determine such an activation condition, logical arithmetic such as AND, OR, NOT or the like may be used. The Boolean model may assume that each connection line (interaction relation) proceeds at the same time. This is the biggest difference between the present invention and ordinary differential equation (ODE) analysis and it may be assumed that reaction times of all connection lines (interaction relation) are identical.

As a detailed analysis method of boolean network analysis, there are a synchronous method and an asynchronous method. The synchronous method identically applies the Boolean role to each node. The synchronous method is a manner that an initially started signal is propagated to a lower node per each step and each node determines activation of each node in accordance with a Boolean role. Due to such characteristics, all boolean models are always in an identical state after a specific simulation. Therefore, when the method is used, boolean models are attracted to an equilibrium state or an attractor.

The asynchronous method supplements the synchronous method which does not explain that biological events occur at different times. The asynchronous method performs temporary update for each connection immediately affecting states of nodes using a stochastic technique. Through this, reaction may be slowed or quickened and thereby identical results are not always obtained. For example, when A affected by L affects F and thereby a reaction rate is reduced to 50%, the biological network analysis device may update biological interaction information between A and F with such information and may simulate the updated information. Alternatively, when a plurality of connection lines is present in a simulation model and a reaction rate increases by 30%, the biological network analysis device may update such information and simulate the updated information.

Figure 6:
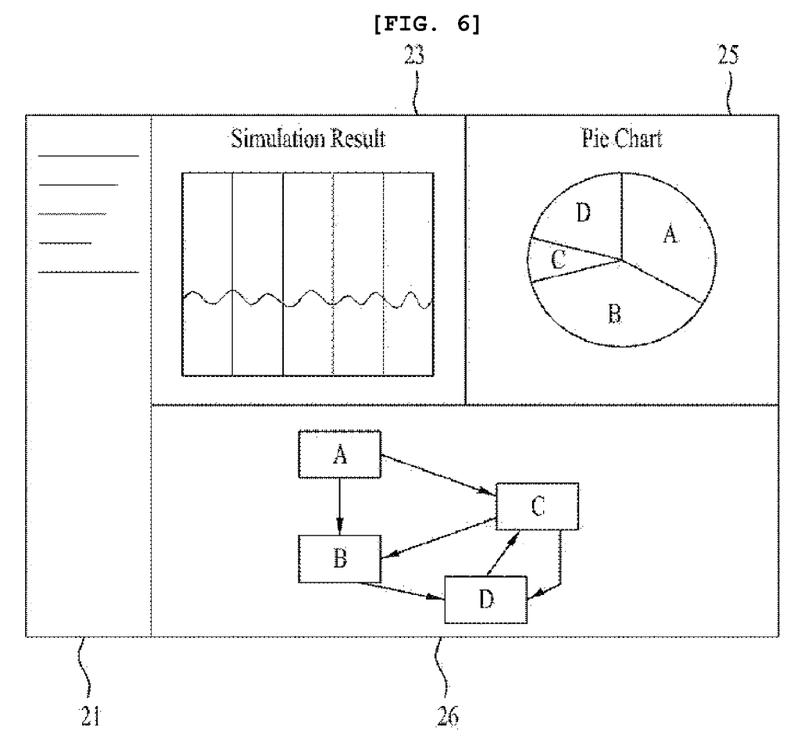
FIG. 6 illustrates an analyzed simulation result according to one embodiment of the present invention analysis.

FIG. 6 illustrates a simulation result analyzed according to one embodiment of the present invention.

Referring to FIG. 6, a simulation result screen may include a directory window 21 representing a file structure, a simulation result window 23, a pie chart window 25 displaying relative amounts of biological objects, and a window 26 displaying a simulation model.

FIG. 6 illustrates an embodiment of a boolean network simulation. Through FIG. 6, it can be confirmed through a simulation result window 23 that protein C vibrates according to time by negative feedback. The negative feedback and positive feedback as one of control mechanisms observed in a biological phenomenon may simply predict the control mechanisms through boolean network analysis.

The present invention automatically generates and simulates a Boolean role which must be designated per node in such an analysis process and thereby may resolve inconvenience that a user must simulate while applying a role.

Figure 7:
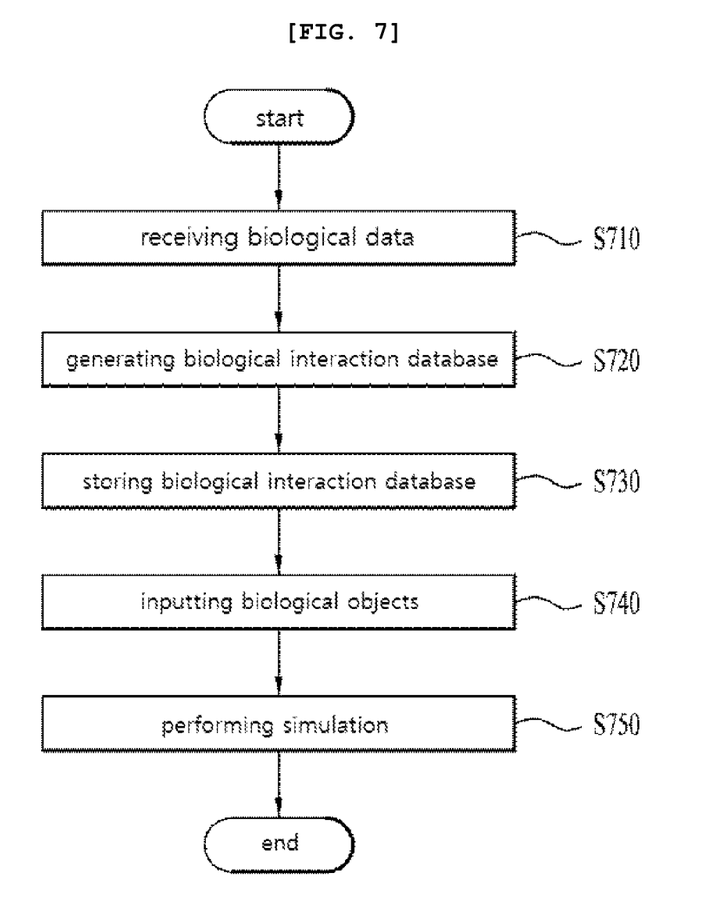
FIG. 7 is a flowchart of a biological network analysis method according to one embodiment of the present invention.

FIG. 7 is a flowchart of a biological network analysis method according to one embodiment of the present invention.

Referring to FIG. 7, the biological network analysis device receives biological data from an external server (S710). The biological data may include biological object information such as proteins, genes, titles of cells and the like, and relation information between biological objects such as activation, suppression, control and the like. The relation information between biological objects is called biological interaction information.

The biological network analysis device extracts biological information from the received biological data to generate a biological interaction database (S720). The biological network analysis device may analyze a sentence structure from the received biological data and may extract biological interaction words and biological object words from the analyzed sentence structure. The biological network analysis device may judge a biological interaction relation between extracted biological object words. The biological network analysis device may extract biological information including biological object information and biological interaction information to generate a biological interaction database.

The biological network analysis device stores the generated biological interaction database (S730). The biological network analysis device receives input of a plurality of biological objects for a simulation (S740).

The biological network analysis device sets each of the input biological objects to a node and automatically generates a Boolean role based on the generated biological interaction database to perform a simulation (S750). The biological network analysis device sets the first node and the second node which receives input from the first node, and may set a Boolean role using interaction information between biological object information of the first node and biological object information of the second node biological. The Boolean role may be individually set in accordance with each node. The biological network analysis device applies a preset probability to perform by updating a connection state between nodes.

The biological network analysis device and a method therefor according to the present invention are not limited to constitutions and methods of embodiments described above and may be variously modified by selectively combining the whole or a portion of each embodiment.

Meanwhile, the biological network analysis method of the present invention may be realized as software stored in a recording medium readable by a processor provided in a biological network analysis device. The recording medium readable by a processor includes all kinds of recording devices in which data readable by a processor is stored. The recording medium readable by a processor is, for example, a ROM, RAM, CD-ROM, magnetic tape, a floppy disk, an optical data storage device or the like. In addition, the recording medium may also be realized in a carrier wave type such as transmission through the Internet. In addition, the recording medium readable by a processor may be distributed in a computer system connected to a network, and thereby code readable by a processor may be stored through a distribution method and may be carried out.

In addition, although the preferred embodiments of the present invention have been disclosed for illustrative purposes, it will be apparent to those skilled in the art that various modifications and variations can be made in the present invention without departing from the spirit or scope of the invention. Thus, it is intended that the present invention covers the modifications and variations of this invention provided they come within the scope of the appended claims and their equivalents.

Mode

As described above, related contents were described in a section of the best modes of the present invention.

INDUSTRIAL APPLICABILITY

As described above, the present invention is entirely or partially applicable to a biological network analysis device and a method therefor.

The invention claimed is:
1. A biological network analysis device comprising:
a communication interface that receives biological data from an external server;
a controller that analyzes a sentence structure from the received biological data, extracts biological object words representing biological object information and biological interaction words representing a biological interaction between biological object information represented by the biological object words from the analyzed sentence structure, determines the biological interaction by using the extracted biological interaction words, derives the biological object information from the extracted biological object words and biological interaction information describing the determined biological interaction, and generates a biological interaction database including the derived biological object information and the derived biological interaction information;

a storage that stores the generated biological interaction database; and an input interface that receives an input of a plurality of biological objects for a simulation, wherein the controller sets each of the input biological objects to each node, generates a Boolean rule between the input biological objects of the each node automatically based on the generated biological interaction database and the input biological objects of the each node, and performs the simulation to control relative amounts of the inputted biological objects of the each node based on the generated Boolean rule.

2. The biological network analysis device according to claim 1, further comprising an output interface to output at least one of the generated biological interaction database or results from the performed simulation.

3. The biological network analysis device according to claim 1, wherein the controller uses a glossary including biological term fields and proteins, genes and cellular names to evaluate the biological interaction between the extracted biological object words using the extracted biological interaction words.

4. The biological network analysis device according to claim 1, wherein the controller sets a first node and a second node receiving input from the first node, and sets Boolean rule using the biological interaction information between biological object information of the first node and biological object information of the second node.

5. The biological network analysis device according to claim 1, wherein the controller individually sets the Boolean rule in accordance with each of the nodes.

6. The biological network analysis device according to claim 1, wherein the controller updates a connection state between the nodes by applying a preset probability to perform the simulation.

7. A method of analyzing a biological network comprising:

receiving biological data from an external server;

analyzing a sentence structure from the received biological data;

extracting biological object words representing biological object information and biological interaction words representing a biological interaction between biological object information represented by the biological object words from the analyzed sentence structure;

determining the biological interaction relation by using the extracted biological interaction words;

deriving the biological object information from the extracted biological object words and biological interaction information describing determined biological interaction;

generating a biological interaction database including the derived biological object information and the derived biological interaction information;

storing the generated biological interaction database;

receiving input of a plurality of biological objects for a simulation;

setting each of the input biological objects to each node;

generating a Boolean rule between the input biological objects of the each node automatically based on the generated biological interaction database and the input biological objects of the each node; and performing the simulation to control relative amounts of the input biological objects of the each node based on the generated Boolean rule.

8. The method according to claim 7, further comprising outputting the generated biological interaction database.

9. The method according to claim 7, further comprising outputting results of the performed simulation.

10. The method according to claim 7, wherein a glossary including biological term fields and proteins, genes and cellular names are used to evaluate the biological interaction relation between the extracted biological object words using extracted biological interaction words.

11. The method according to claim 7, wherein the performing of the simulation includes setting a first node and a second node receiving input from the first node, and sets the Boolean rule using biological interaction information between biological object information of the first node and biological object information of the second node.

12. The method according to claim 7, wherein the performing of the simulation includes individually setting the Boolean rule in accordance with each of the nodes.

13. The method according to claim 7, wherein the performing of the simulation includes updating a connection state between nodes by applying a preset probability to perform the simulation.

14. The biological network analysis device according to claim 1, wherein the biological object words correspond to words for at least one type of proteins, at least one type of genes, or at least one name for cells.

15. The biological network analysis device according to claim 3, wherein the glossary includes Metamap and Abner.

16. The method according to claim 7, wherein the biological object words correspond to words for at least one type of proteins, at least one type of genes, or at least one name for cells.

17. The method according to claim 10, wherein the glossary includes Metamap and Abner.

* * * * *